(12) United States Patent
Horino et al.

(10) Patent No.: US 6,200,580 B1
(45) Date of Patent: *Mar. 13, 2001

(54) POWDERED BASE MATERIAL TREATED WITH ORGANIC SILICON COMPOUNDS AND THEIR METHOD FOR PRODUCING

(75) Inventors: Masaakira Horino, Sagamihara; Hideki Takahashi, Saitama, both of (JP)

(73) Assignee: Miyoshi Kasei, Inc., Saitama (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/149,797

(22) Filed: Sep. 9, 1998

(30) Foreign Application Priority Data

Sep. 10, 1997 (JP) .................................................. 9-262735
Aug. 5, 1998 (JP) ................................................ 10-221551

(51) Int. Cl.$^7$ ...................................................... A61K 6/00
(52) U.S. Cl. .......................... 424/401; 424/59; 424/70.9; 424/70.12; 424/641; 424/642
(58) Field of Search ........................... 424/401, 59, 70.9, 424/70.12, 641, 642

(56) References Cited

U.S. PATENT DOCUMENTS

| | | |
|---|---|---|
| 5,032,390 | * 7/1991 | Iwaya et al. ........................... 424/59 |
| 5,744,126 | * 4/1998 | Horino et al. ......................... 424/59 |

FOREIGN PATENT DOCUMENTS 0 665 004   8/1995   (EP) .
0 799 865  10/1997   (EP) .
7-196946 * 8/1995   (JP) .

OTHER PUBLICATIONS

Database WPI, Abstract for J09030917 (Feb. 4, 1997), Derwent Publications, Ltd., London GB.

* cited by examiner

*Primary Examiner*—Thurman K. Page
*Assistant Examiner*—Lakshmi Channavajjala
(74) *Attorney, Agent, or Firm*—Armstrong, Westerman, Hattori, McLeland & Naughton, LLP (57) ABSTRACT

A powdered base material treated with organic silicon compounds comprised of a powdered base material to which is preferably affixed one or more of metal hydroxides, hydroxy group-containing inorganic oxides and the gelated products thereof and to which are also affixed a reactive alkyl polysiloxane and a methyl hydrogen polysiloxane, preferably the methyl hydrogen polysiloxane represented by the following formula:

$$(CH_3)_3SiO[(CH_3)_2SiO]_m(CH_3HSiO)_nSi(CH_3)_3,$$

wherein m and n are each an integer, and m+n=7 to 50, more preferably 7 to 25 and m:n =1:0.2 to 1:4, more preferably m:n=1:0.5 to 1:2. The obtained powdered base material treated with organic silicon compounds is superior in adhesion to the skin, free from flocculation, particularly smooth and soft to touch, has a color tone extremely high in saturation (good color extension ) when used in conjunction with a colored pigment and is also superior in hydrophobic properties and water-proofness without losing the characteristics of being free from residual hydrogen, and the properties of high safety and high quality.

11 Claims, 1 Drawing Sheet

FIG.1

POWDERED BASE MATERIAL TREATED WITH ORGANIC SILICON COMPOUNDS AND THEIR METHOD FOR PRODUCING

BACKGROUND OF THE INVENTION

1. Field of the Invention

The present invention relates to a powdered base material treated with organic silicon compounds, a method for producing a powdered base material treated with organic silicon compounds, and a cosmetic comprising the powdered base material treated with organic silicon compounds. The powdered base material treated with organic silicon compounds according to the present invention can be used as additives for resins, paints, and the like, in addition to cosmetics.

2. Description of the Related Art

Heretofore, a pigment surface-treated with an organic silicon compound, such as methyl hydrogen polysiloxane, is excellent in repellence, and is recently used extensively in two-way cake type cosmetic or powdered foundation for the purpose mainly of preventing makeup collapsing.

In JP Patent Kokai Publication JP-A-7-196946 is disclosed a pigment treated with an organic silicon compound in which a straight-chain reactive alkyl polysiloxane has been adsorbed with orientation under heating treatment to a pigment in the surface, and in which the reactive alkyl polysiloxane is a straight-chain reactive alkyl polysiloxane having a polymerization degree of 25 to 100 and a ratio (Mw/Mn) of the weight average molecular weight (Mw) to the number average molecular weight (Mn) of 1.0 to 1.3, with one of the terminals of the molecular chain carrying at least one of an alkoxy group, a hydroxy group, a halogen atom, an amino group, and an imino group.

1. Problem to be Solved by the Invention

In the course of the completion to the present invention, the following problems have been also found by the present invention.

The pigment treated with the organic silicon compound, such as methyl hydrogen polysiloxane, suffers from the following problems:

It is noted that the conventional methyl hydrogen polysiloxane, such as KF99 manufactured by SHIN-ETSU KAGAKU KOGYO KK, TSF484 manufactured by TOSHIBA SILICONE KK or SH1107 manufactured by TORAY DOW-CORNING KK, undergo cross-linking polymerization reaction, and that, since methyl hydrogen polysiloxane which has covered the surface of the powdered pigment assumes a reticulate three-dimensional structure, it is progressively converted to resin, thus generating a sole silicone resin, or causing granulation or flocculation of the powdered pigment particles. Thus, the conventional pigment treated with the organic silicon compound has a rough or coarse feeling in use.

(CH$_3$)$_3$SiO(CH$_3$HSiO)$_n$Si(CH$_3$)$_3$      (4)

wherein n is an integer of 30 to 40.

On the other hand, the structure of routinely employed methyl hydrogen polysiloxane is as shown in the above general formula (4). Since methyl hydrogen polysiloxane having this structure has a functional group in each siloxane unit, it is subject to steric hindrances on thermal polymerization to render the progress of the reaction difficult. Thus, a large quantity of non-reacted hydrogen atoms are left in the methyl hydrogen polysiloxane molecules.

If the powdered pigment surface-treated with this methyl hydrogen polysiloxane is mixed into a cosmetic, residual hydrogen is produced by alkaline materials contained in the cosmetic to give rise to such phenomenon in which, in the case of an emulsified product, the vessel for the cosmetic tends to be expanded or destroyed and, in the case of a powdered article, above all pressed goods, the solidified state is embrittled and crushed to pieces. Also, in the manufacturing process for the cosmetic, a residual hydrogen gas tends to be yielded under alkaline or acidic conditions thus causing the risk of explosion during manufacture or causing a safety problem to the user.

Moreover, since the main skeleton is comprised of methyl hydrogen siloxane, the main chain has a decreasing degree of freedom with progress in polymerization, such that the produced coating is hard and brittle while tending to be cracked. Thus, the pigment treated with the organic silicon compound, obtained upon coating the powdered pigment with this methyl hydrogen polysiloxane followed by polymerization, experiences a problem of lowered crushing strength or lowered water-proof properties due to the low crushing strength and the high rate of coating destruction.

The pigment treated with the organic silicon compound, in which the above-mentioned specified straight-chain reactive alkyl polysiloxane is oriented and adsorbed to the pigment surface by heat processing, as disclosed in JP Patent Kokai Publication JP-A-7-196946, overcomes the above-mentioned problem. That is, with the pigment treated with the organic silicon compound described in the above publication, as contrasted with the pigment in which methyl hydrogen polysiloxane has undergone cross-linking polymerization reaction to form a resin film as described above, the above-mentioned specified reactive alkyl polysiloxane coated on the surface of the powdered cosmetic is heated and thereby the straight-chain alkyl polysiloxane is present affixed to the powdered pigments in the oily state, there is therefore no risk of flocculation of the particles of the powdered pigments, thus assuring excellent feeling to the touch, adhesion to skin and good color extension.

However, it has not been possible with the pigment treated with the organic silicon compound, obtained on heating with the above-mentioned specified reactive alkyl polysiloxane, to realize optimum hydrophobic properties or water-proofness for starting materials for the cosmetic, in particular for pearl pigments such as hydrated yellow iron oxide, iron oxide, titanium oxide or titanium mica.

The fact that the pigment treated with the organic silicon compound, obtained on reacting with the specified reactive alkyl polysiloxane, as described in the above-mentioned publication, is not sufficient in hydrophobic properties or in water-proofness, is manifested particularly significantly when the pigment treated with the organic silicon compound is mixed into an emulsion of emulsion-type cosmetic, such as cream foundation or liquid foundation. Specifically, in the emulsion type cosmetic, the above-mentioned pigment exhibiting the relatively strong adhesion properties of the reactive alkyl polysiloxane shifts to the oily phase, while the pigment exhibiting relatively weak adhesion shifts to the aqueous phase, thus leading to color separation or separation of the cream foundation or li quid foundation to cause problem, in particular, in the emulsion type foundation of cosmetic.

It is therefore an object of the present invention to overcome the above-mentioned problems of the related arts, and to provide a powdered base material treated with an organic silicon compound exhibiting superior adhesion to the skin and particularly smooth feeling to the touch, free of flocculation, exhibiting color hue ( tone ) of extremely high saturation (good color extension properties) when combined with a colored pigment, and which is superior in hydrophobic properties and water-proofness, without loss of the desirable characteristics of freedom from residual hydrogen, high safety and high quality when used in conjunction with colored pigments. It is another object of the present invention to provide a method for producing the powdered base material and the cosmetic containing the powdered base material treated with an organic silicon compound.

SUMMARY OF THE INVENTION

In view of the above-mentioned problems, the present inventors conducted perseverant research, and found that, by heating a powdered base material, in particular a coated powder, comprised of a powdered base material, such as a pigment, the surface of which is coated with at least one substance selected from the group consisting of metal hydroxides, hydroxy group-containing inorganic oxides and the gelated products (gels) thereof, with a reactive alkyl polysiloxane in the presence of a methyl hydrogen polysiloxane having a specific polymerization degree and a specific proportion of dimethyl siloxane units, the properties of the pigment treated with the organic silicon compounds, such as adhesion to the skin and smoothness, obtained by reacting with the reactive alkyl polysiloxane disclosed in the above-mentioned JP Patent Kokai Publication JP-A-7-196946 can be retained, while the hydrophobic properties and water-proofing properties proper to the obtained treated pigment can be further improved, and found that the coated film in the obtained treated powdered base material can further be improved in performance. This finding has led to completion of the present invention.

Specifically, in one aspect, the present invention can achieve the above purpose by providing a powdered base material treated with organic silicon compounds comprising a powdered base material to which two organic silicon compounds, that is a reactive alkyl polysiloxane and a methyl hydrogen polysiloxane, preferably the polysiloxane (1), more preferably the polysiloxane (2), and further more preferably the polysiloxane. (3), respectively represented by the following general formula are firmly affixed:

(1)

wherein m and n are each an integer;

(2)

wherein m and n are each an integer; m+n=7 to 50, and m:n=1:0.2: to 1:4; and (3)

wherein m and n are each an integer; m+n=7 to 25, and m:n=1:0.5: to 1:2.

As a powdered base material for treating the two organic silicon compounds therewith, a compound powdered base material comprised of at least one substance selected from the group of metal hydroxides, hydroxy group-containing inorganic oxides and the gels thereof affixed to a powdered base material may be employed.

The reactive alkyl polysiloxane may be a straight-chain reactive alkyl polysiloxane having a polymerization degree of 25 to 100, and a ratio of the weight average molecular weight (Mw) to the number average molecular weight (Mn), Mw/Mn, of 1.0 to 1.3, and wherein one of the terminals of the molecular chain may carry at least one of an alkoxy group, a hydroxy group, a halogen atom, an amino group and an imino group.

The ratio of the weight (H) of the reactive alkyl polysiloxane to the weight (F) of the powdered base material, H/F, ranges between 0.1/100 and 30/100.

The ratio of the weight (M) of the methyl hydrogen polysiloxane to the weight (F) of the powdered base material, M/F, ranges between 0.1/100 and 5/100.

The ratio of the total weight (K) of the metal hydroxides, hydroxy group-containing inorganic oxides and the gels thereof affixed to the compound powdered base material, to the weight (F) of the powdered base material before compounding them, K/F, ranges between 0.1/100 and 10/100.

In a second aspect, the present invention can also achieve the above purpose by providing a method for producing a powdered base material treated with organic silicon compounds comprising the step of thermally reacting a reactive alkyl polysiloxane and a methyl hydrogen polysiloxane, for example, one preferably represented by the above formula (1), more preferably (2), and further more preferably (3), with a powdered base material, for affixing the reactive alkyl polysiloxane and the methyl hydrogen polysiloxane to the powdered base material.

In a third aspect, the present invention can also achieve its purpose by providing a cosmetic comprising the powdered base material treated with organic silicon compounds as defined above.

It is noted that in the methyl hydrogen polysiloxane of the type specified in the present invention, into which is introduced the dimethyl siloxane units, shown by the above general formula (1), since the main chain is improved in the degree of freedom because the dimethyl siloxane units $(SiCH_3CH_3O)_m$ have no reactivity, the coat of the obtained powdered base material treated with organic silicon compounds is flexible as compared to the coat as obtained using conventional methyl hydrogen polysiloxane, and thus is not prone to cracking.

It is noted that, since in the methyl hydrogen polysiloxane employed typically in the present invention, as compared to conventional methyl hydrogen polysiloxane, the proportion of the methyl hydrogen siloxane units $(SiHCH_3O)_n$ is lowered, condensation is retarded, as a result of which stronger reaction conditions (those with the powdered base material) than those for methyl hydrogen polysiloxane not having the dimethyl siloxane unit are required.

The numerical ranges given herein include not only both extreme values but also any intermediate values.

DETAILED DESCRIPTION OF THE PREFERRED EMBODIMENTS

Powdered Base Material Treated with Organic Silicon Compounds

The powdered base material treated with organic silicon compounds according to the present invention is a powdered base material having a reactive alkyl polysiloxane and a methyl hydrogen polysiloxane, preferably represented by the above formula (1) to (3) and defined therein, affixed thereto by physical adsorption or adhesion, by orientation adsorption, by a variety of chemical reactions, such as condensation, polycondensation reactions, and the like.

It is noted that the reactive alkyl polysiloxane and the methyl hydrogen polysiloxane, preferably represented by the above formula (1) to (3), can be affixed as a coating layer (an outermost coating layer) to part or all of the surface of the powdered base material (or a compound powdered base material comprised of at least one substance selected from the group consisting of metal hydroxides, hydroxy group-containing inorganic oxides and the gelated products (gels) thereof affixed to the powdered base material). Meanwhile, when the reactive alkyl polysiloxane and the methyl hydrogen polysiloxane as mentioned above, for example, preferably the polysiloxane represented by the above general formula (1) to (3), are fixed to the compound powdered base material, a powdered base material which is superior in smoothness, hydrophobic property, water resistance and safety can be obtained.

The reactive alkyl polysiloxane and hydrogen polysixolane can be affixed directly to the surface of the compound powdered base material.

Powdered Base Material

The powdered base material used in the present invention includes an organic and inorganic powdered base material, which in turn includes a pigment. The pigment includes an extender, a compound powdered pigment, a white pigment, a colored pigment, a pearl pigment and the like. The mean particle size of the powdered base material is preferably 0.01 to 100 $\mu$m, more preferably 0.01 to 30 $\mu$m and further more preferably 0.01 to 15 $\mu$m.

The extender includes, for example, an inorganic material, such as talc, kaoline, sericite, muscovite, phlogopite, lepidolite, synthetic mica, lithia mica, vermiculite, magnesium carbonate, calcium carbonate, diatomaceous earth, magnesium silicate, calcium silicate, aluminum silicate, silica, hydroxy apatite, zeolite, boron nitride, barium sulfate, and alumina, nylon powder, polyethylene powder, benzo guanamine powder, Teflon™ powder (ethylene tetrafluoride), polystyrene powder, cellulose powder, silk powder, epoxy powder, silicone powder, methyl polymethacrylate powder and starch.

The compound powdered pigment includes, for example, titanium oxide-iron oxide, titanium oxide-silica, sericite-titanium oxide, silica-cerium oxide, silica-zinc oxide, mica-aluminum hydroxide, mica-titanium oxide-silica, mica-iron oxide-silica, titanium oxide-iron oxide-silica, barium sulfate-titanium oxide, barium sulfate-zinc oxide, mica-barium sulfate-titanium oxide, mica-barium sulfate-zinc oxide, and the like.

The white pigment includes, for example, titanium oxide, zinc oxide, cerium oxide and the like. The colored pigment includes, for example, an inorganic pigment, such as iron oxide, hydrated iron oxide, loess, mango violet, cobalt violet, chromium oxide, chromium hydroxide, cobalt titanate, ultramarine and Berlin blue. The organic pigment includes, for example, tar dyes authorized for use, such as zirconium, barium and aluminum lake, e.g., Red-201, Red-202, Red-204, Yellow-4, Yellow-5 and Blue-1, and natural dyes, such as β-carotene, chlorophyll or cotinyl.

The pearl pigment includes, for example, titanium oxide coated mica, titanium oxide coated bismuth oxychloride, titanium oxide coated talc, bismuth oxychloride, ichthyosis, aluminum powder and the like.

The powdered base material to be treated with two types of organic silicon compounds in the present invention, is preferably a compound powdered base material comprised of at least one substance selected from the group consisting of metal hydroxides, hydroxy group-containing inorganic oxides and the gels thereof affixed to a powdered base material.

Preferably, the compound powdered base material is one comprised of at least one substance selected from the group consisting of metal hydroxides, hydroxy group-containing inorganic oxides and the gels thereof affixed to a powdered base material so as to form a coating layer (first coating layer).

The above-mentioned first coating layer can be formed to cover part or all of the powdered base material. That is, the compound powdered base material is prepared by affixing at least one or more of the metal hydroxides, the hydroxy group-containing inorganic oxides and the gels thereof to part or all of the surface of the powdered base material, preferably on all of the surface on the powdered base material, to form the first coating layer on part or all of the surface of the powdered base material.

The amount of the metal hydroxide(s), the hydroxy group-containing inorganic oxide(s) and/or the gel(s) thereof affixed to the powdered base material in the compound powdered base material is 0.1 to 10 wt %, preferably 0.5 to 5.0 wt % and more preferably 1.0 to 2.0 wt %.

If the above amount is less than 0.1 wt %, the powdered base material treated with organic silicon compounds having sufficient hydrophobic properties and water-proofness is not likely to be produced.

If the above amount exceeds 10 wt %, it is not likely that hydrophobic properties and water-proofness exceeding those obtained with 10 wt % cannot be obtained. In addition, the powdered base material treated with organic silicon compounds tends to be inferior in feeling to the touch. Therefore, it is not preferable to exceed 10 wt %.

The metal hydroxide includes, for example, hydroxide of a metal, such as aluminum, calcium, magnesium, zinc, titanium, zirconium, cerium, iron, cobalt, manganese and nickel, such as $Al(OH)_3$, $Ca(OH)_2$, $Mg(OH)_2$, $Zn(OH)_2$, $Ti(OH)_4$, and the like.

The hydroxy group-containing inorganic oxide includes, preferably for example, hydroxy group-containing metal oxides, such as hydroxy group-containing oxide of a metal, such as aluminum, zinc, titanium, iron, magnesium, calcium and the like. Thus, the hydroxy group-containing inorganic oxide may be, for example, $AlO \cdot OH$, $ZnO \cdot OH$, $FeO \cdot OH$, $TiO \cdot (OH)_2$, and the like.

As a method for producing the compound powdered base material by affixing one or more of the metal hydroxides, the hydroxy group-containing inorganic oxides and the gels thereof to the surface of a powdered base material, an example is a method comprising the step of dispersing the powdered base material in a solution obtained by dissolving at least one water-soluble inorganic metal salt (such as aluminum chloride, aluminum sulfate, magnesium chloride and the like) in a solvent (aqueous solvent, such as water and the like), adding to this liquid dispersion at least one inorganic hydroxide, such as sodium hydroxide, potassium hydroxide and the like, for neutralization, and affixing at least one of the metal hydroxides, hydroxy group-containing inorganic oxides and gels thereof to the surface of the powdered base material. In this method, the above-mentioned solution may be warmed, if necessary, to 50 to 100.

Reactive Alkyl Polysiloxane

The reactive alkyl polysiloxane used in the present invention is preferably a straight-chain reactive alkyl polysiloxane. More preferably, this reactive alkyl polysiloxane satisfies one or more (preferably two or more and more preferably all) of the following conditions (1) to (3):

(1) only one terminal end of a molecular chain carrying one reactive species selected from an imino group and an amino group ($NH$, $NH_2$), halogen atom (Cl, Br, I), hydroxy group (OH), and alkoxy group (OR, wherein R is an alkyl group, for example, an alkyl having 1 to 5 carbons);

(2) a polymerization degree of 25 to 100, preferably 30 to 60, and more preferably 30 to 50; and (3) a ratio of the weight average molecular weight (Mw) to the number average molecular weight (Mn), Mw/Mn being 1.0 to 1.3.

This reactive alkyl polysiloxane can be produced by, for example, a method for production disclosed in the JP patent Kokai Publication JP-A-7-196946, the contents of which are incorporated in this specification by reference.

It is noted that the above-mentioned reactive alkyl polysiloxane has preferably a polymerization degree of 25 to 100, more preferably 30 to 60, and more preferably 30 to 50. If the above-mentioned polymerization degree is less than 25, the water-repellent effect and smoothness tend to be inferior such that the characteristics of silicone are occasionally not displayed. If the above-mentioned polymerization degree exceeds 100, the reactivity with respect to the surface of the powdered base material, the metal hydroxide, the hydroxy group-containing inorganic oxide or the gel thereof affixed, or the orientation adsorbing power tend to be inferior, possibly because of steric hindrances.

The above-mentioned ratio of the weight average molecular weight (Mw) of the reactive alkyl polysiloxane to number average molecular weight (Mn), Mw/Mn, generally referred to as molecular weight dispersion degree, is preferably 1.0 to 1.3 in the present invention. That is, the reactive alkyl polysiloxane having the molecular weight dispersion degree less than 1.0 theoretically cannot exist, whereas, if the molecular weight dispersion degree exceeds 1.3, the molecular weight distribution is spread extensively such that, when the reactive alkyl polysiloxane is affixed to the powdered base material, such as by chemical reaction, the smooth feel upon use which is the aim of the present invention occasionally cannot be obtained. The molecular weight dispersion degree can be determined by, for example, gel permeation chromatography (GPC) and the like.

A desirable reactive alkyl polysiloxane usable in the present invention is represented by, for example, one of the following chemical formulae (5) and (6):

$$R(R_2SiO)nSiR_{3-m}(YX)_m \quad (5)$$

$$[R(R_2SiO)_nSiR_2]_2NH \quad (6)$$

In the above formula, all the R present in the above formulae may be independently an alkyl group, such as methyl, ethyl, propyl group, and the like, X denotes one of an amino group, an imino group, a halogen atom, a hydroxy group and alkoxy group, Y denotes a direct coupling, namely direct coupling between neighboring Si and X with no Y, or denotes a bivalent hydrocarbon group, such as methylene group, ethylene group, butylene group, and the like, with hydrogen atom(s) of the hydrocarbon group being optionally replaced by other substitutent(s), such as a hydroxy group, a methoxy group, an ethoxy group, an ethyl group, a methyl group, and the like, m denotes an integer of from 1 to 3 and n denotes an integer of from 25 to 100, preferably 30 to 60 and more preferably 30 to 50.

Examples of such alkyl polysiloxane include dimethyl polysiloxysilazane, α-monohydroxy siloxane, α,ω-dihydroxy polydimethyl siloxane, α-monoalkoxy polydimethyl siloxane, α-dialkoxy polydimethyl siloxane, α-trialkoxy polydimethyl siloxane, α,ω-dialkoxy dimethyl polysiloxane, α,ω-hexaalkoxy polydimethyl siloxane, dimethyl polysiloxy chloride, dimethyl polysiloxy bromide, dimethyl polysiloxy iodide, and the like. Of these, α-monoalkoxy polydimethyl siloxane, α-dialkoxy polydimethylsiloxane and α-trialkoxy polydimethylsiloxane, such as α-triethoxy polydimethyl siloxane, are desirable since these are highly satisfactory in reactivity and can give smooth feeling to the touch.

The amount of the above-mentioned reactive alkyl polysiloxane mixed in the powdered base material treated with organic silicon compounds according to the present invention is usually in a range of 0.1 to 30 wt %, preferably 0.3 to 10 wt %, more preferably 0.5 to 6 wt % and most preferably 0.5 to 3 wt % to the total weight of the powdered base material to be used or the above-mentioned compound powdered base material, if it is used as the powdered base material, depending on the particle size or the specific surface area of the powdered base material to be treated. If the amount is less than 0.1 wt %, excellent feeling to the touch, adhesion to skin, color extension or the inhibition of flocculation of particles, and the characteristic of reactive alkyl polysiloxane, occasionally cannot be obtained. If the amount of addition exceeds 30 wt %, the powder tends to be excessively wet, displays poor extendability, and is affixed only sporadically to the skin, because the excess reactive alkyl polysiloxane relative to the specific surface area of the powders does not affix to the powders on the surface thereof. So, excess reactive alkyl polysiloxane is not preferable.

Methyl Hydrogen Polysiloxane

In particular, one or more of the structures shown in the following formula (1), more preferably formula (2) and further more preferably formula (3), can be selected and used as the methyl hydrogen polysiloxane in the present invention.

$$(CH_3)_3SiO[(CH_3)_2SiO]_m(CH_3HSiO)_nSi(CH_3)_3 \quad (1)$$

wherein m and n are each an integer;

$$(CH_3)_3SiO[(CH_3)_2SiO]_m(CH_3HSiO)_nSi(CH_3)_3 \quad (2)$$

wherein m and n are each an integer; m+n=7 to 50, and m:n=1:0.2: to 1:4; and $$(CH_3)_3SiO[(CH_3)_2SiO]_m(CH_3HSiO)_nSi(CH_3)_3 \quad (3)$$

wherein m and n are each an integer; m+n=7 to 25, and m:n=1:0.5: to 1:2.

The amount of addition (affixing amount) of the above-mentioned specified methyl hydrogen polysiloxane in the powdered base material treated with organic silicon compounds according to the present invention is generally 0.1 to 5 wt %, preferably 0.1 to 3 wt %, more preferably 0.3 to 2 wt %, and further more preferably 0.5 to 1.0 wt %, based on the powdered base material (above-mentioned compound powdered base material in case it is used as the powdered base material). If the amount of addition is less than 0.1 wt %, the hydrophobic properties and water-proofness, in particular, tend to be unchanged from those obtained when using the reactive alkyl polysiloxane alone, such that the effect of using the above-mentioned methyl hydrogen polysiloxane having the specified polymerization degree and the dimethyl siloxane units in the specified proportion is not displayed. If the amount of addition exceeds 5 wt %, there is no change in hydrophobic properties and water-proofness and, much residual hydrogen is present, such that use in excess of this upper limit is not only uneconomical but also tends to lower significantly the excellent feeling to the touch characteristic of the reactive alkyl polysiloxane.

The above-mentioned specified methyl hydrogen polysiloxane affixed to the powdered base material, in particular the above-mentioned compound powdered base material, in the powdered base material treated with organic silicon compounds according to the present invention, is substantially free of residual H-group. However, the above-mentioned specified methyl hydrogen polysiloxane, affixed to the powdered base material, in particular the above-mentioned compound powdered base material, in the powdered base material treated with organic silicon compounds according to the present invention, can have five or less (preferably three or less and more preferably one or less) residual H-group(s) for one of those shown in the above general formula (1) and defined therein.

The research by the present inventors has revealed that of the silicones, KF9901 manufactured by SHIN-ETSU KAGAKU KK, represented by the following formula (7), has its main component similar to those from the above-mentioned specified methyl hydrogen polysiloxane, and is poor in reactivity, that is it is less prone to cross-linking polymerization reaction. Since it contains at least a quantity of the above-mentioned specified methyl hydrogen polysiloxane according to the present invention, it can be used with advantage for the present invention.

$(CH_3)_3SiO[(CH_3)_2SiO]_m(CH_3HSiO)_nSi(CH_3)_3$     (7)

wherein m and n are each an integer, and m+n=20 to 30 and m=10 to 15.

Since silicone is a high polymer, it exhibits molecular weight distribution. When the methyl hydrogen polysiloxane having the specified structure in the present invention is contained therein, for example, as the molecular structure constituting the center of the molecular weight distribution, the purpose for the present invention is satisfied.

The powdered base material treated with organic silicon compounds according to the present invention can be put to the usage for which the conventional powdered base material has been used, such as cosmetics, resins, paints, and the like.

Method for Production of Powdered Base Material Treated with Organic Silicon Compounds A method for producing a powdered base material treated with organic silicon compounds according to the present invention is a method comprising the step of thermally reacting a reactive alkyl polysiloxane and a methyl hydrogen polysiloxane represented by the above-mentioned formula (1) with a powdered base material, in particular a compound powdered base material comprised of at least one substance selected from the group consisting of metal hydroxides, hydroxy group-containing inorganic oxides and the gels thereof affixed to a powdered base material, for affixing the reactive alkyl polysiloxane and the methyl hydrogen polysiloxane to the powdered base material (or the compound powdered base material).

For heating the above-mentioned reactive alkyl polysiloxane and the above-mentioned specified methyl hydrogen polysiloxane with the powdered base material, in particular with the compound powdered base material, heating as a mixture may be carried out. It is possible for the solvent to be contained in the mixture. Specifically, the above-mentioned reactive alkyl polysiloxane, the above-mentioned specified methyl hydrogen polysiloxane and the powdered base material, in particular the compound powdered base material, can be dispersed in a solvent and heated for affixing the reactive alkyl polysiloxane and the specified methyl hydrogen polysiloxane to the above-mentioned powdered base material, in particular the compound powdered base material.

For mixing and dispersing the following three substances:
(i) a compound powdered base material obtained by affixing one more of metal hydroxides, hydroxy group-containing inorganic oxides and the gels thereof to a powdered base material;
(ii) a reactive alkyl polysiloxane; and
(iii) the above-mentioned specified methyl hydrogen polysiloxane having the specified proportion of the dimethylsiloxane units and the specified polymerization degree, the solvent which can be used is a combination of water with an organic solvent, preferably an organic solvent and preferably an organic solvent in which the above-mentioned reactive alkyl polysiloxane can be dissolved.

The above-mentioned organic solvent may be selected taking sufficiently into account surface activity and thermal stability of the powdered base material to be surface-treated and the inflammation point of the organic solvent itself. Examples of the solvent include ethers, ketones, halogenated hydrocarbons, aliphatic hydrocarbons and alcohols, such as ethyl alcohol, isopropyl alcohol, n-butanol, hexane, toluene, xylene, methylethylketone and the like.

The organic solvent may be used in an amount of 1 to 100 wt % based on the total weight of the powdered base material, or the above-mentioned compound powdered base material when it is used. Since the cost of the organic solvent is reflected in the cost of the ultimate product, the solvent is preferably used in such an amount as maximizes the effect for the minimum amount. The solvent is used in an amount preferably of 20 to 70 wt % and more preferably of 20 to 50 wt % based on the total weight of the powdered base material or the compound powdered base material when used. If the amount of the organic solvent is less than 20 wt %, the reactive alkyl polysiloxane tends to fail to be uniformly permeated in the surface of the powdered base material or the compound powdered base material, to render it difficult to obtain sufficient hydrophobic properties and water-proofness.

The desirable condition for thermally reacting the mixture of the powdered base material, or the compound powdered base material when it used, and the above-mentioned reactive alkyl polysiloxane and the methyl hydrogen polysiloxane include the heating temperature of 60 to 200° C. and the heating time of 0.5 to 12 hours. If the beating is conducted at a temperature lower than 60° C., the process of adhesion is delayed significantly, which is an economic disadvantage. If the heating temperature exceeding 200° C. is used, not only is the equipment cost raised, but also the hydrophobic properties and the water-proofness of the ultimate product, that is the powdered base material treated with organic silicon compounds, are not improved over those of the product obtained by thermally reacting at 200° C. Therefore, heating at a temperature exceeding 200° C. is not desirable in view of costs. The temperature range desirable in view of economic profitability is 80 to 160° C., and more preferably 90 to 140° C.

The more desirable heating time is 1 to 12 hours. The heating temperature is suitably set depending on the types of powdered base material employed. It is set to a lower value for the organic powdered base material. In this case, the heating time needs to be longer. The inorganic powdered base material is desirable in that the process of adhesion, alcohol removing reaction, polymerization reaction and polycondensation reaction is accelerated to a shorter time. The heating can be carried out desirably for 1 to 12 hours for obtaining a more tightly adhered product even after distilling off the solvent under normal or reduced pressure. The heating time is more preferably 1.0 to 8 hours, and further more preferably 1.0 to 4 hours.

Cosmetic

The cosmetic of the present invention comprises one or more of the above-mentioned powdered base materials treated with organic silicon compounds according to the present invention. There is no particular limitation on the configuration of the cosmetic in the present invention. Examples for the cosmetic of the present invention include white powders or non-aqueous foundation, such as powder foundation, moist powder foundation (oil-rich product), oily foundation spots cover, cover mark, compact powder, two-way cake, face powder and perspiration suppressing sprays, a point-making cosmetic, such as eye shadow, powder brusher, mascara, lipsticks, lip gloss, eye-brow pencils eye-liners and nail colors, emulsifier-type products, such as emulsifier-type foundation and under-makeup base, a basic cosmetic, such as powder pack, cleansing pack, sun-screen cream and a lotion cosmetic, and full-body products, such as baby powders, body powders and flagrance powders.

It is also possible to add oiliness agents, powders, solvents, surfactants, UV absorbers, antiseptics, bactericides, moisture keeping agents, vitamins and/or perfumes usually used for all varieties of cosmetics, into the cosmetics in the present invention, for achieving the purpose of the present invention, and the thus obtained cosmetics are within the scope of the present invention.

Examples of the oiliness agents in this case include higher fatty acids, higher alcohols, synthetic esters, wax, vegetable oils, animal fats, hydrocarbons, fluorocarbons, perfluoroether, fluoro alkoxy phosphasen, and the like.

Examples of the silicone oils include dimethyl polysiloxane, methyl phenyl polysiloxane, polyether modified silicone, fluorine modified silicone, methyl cetyl modified silicone, amino modified silicone, cyclic dimethyl polysiloxane and the like.

The powders may be those routinely employed for cosmetics. Examples of the powders include talc, kaolin, sericite, muscovite, synthetic mica, calcium silicate, magnesium silicate, silica, an hydroxy apatite, and the like.

Examples of the resin powders include nylon powders, polyethylene powders, powders of methyl polymethacrylate, polystyrene powders, powders of vinyl acetate, and the like. The organic powders, such as silk powders, cellulose powders and starch may be employed. These powders may or may not be surface-treated with a coupling agent, silicone, fluorine, amino acid, metal soap, collagen, lecithin, plasma, and/or the like.

As the solvents, those routinely used for cosmetics, such as water, alcohol, 1,3 butylene glycol, propylene glycol, polyethylene glycol, and the like, as well as a cyclic silicone, may be used.

As for the surfactants used, they include anionic surfactants, nonionic surfactants, amphoteric surfactants and cationic surfactants.

The desirable amount of the powdered base material treated with organic silicon compounds according to the present invention to be used in the cosmetic of the present invention is 1 to 100 wt %, based on the total weight of the cosmetic set to 100 wt %, 1 to 100 wt %, based on the total weight of the powder used therein, and 1 to 60 wt %, based on the total weight of the emulsified product, in the case of the powdered cosmetic, the cake-shaped cosmetic or the kneaded cosmetic, and the emulsified cosmetic, respectively.

Operations and Performances

The powdered base material treated with organic silicon compounds of the present invention is superior in adhesion to skin, free from flocculation, particularly smooth and excellent in feeling to the touch, extremely low in the amount of residual hydrogen, and superior in hydrophobic properties and water-proofness, while having color tone of extremely high saturation ( good color extension ) when the powdered base material is used in conjunction with colored pigment.

More specifically, in the pigment treated with organic silicon compounds obtained by thermal reaction with the above mentioned reactive alkyl polysiloxane disclosed in JP patent Kokai Publication JP-A-7-196946, and having an alkoxy group at a terminal of a molecular chain of the above-mentioned reactive alkyl polysiloxane, if the above-mentioned reactive alkyl polysiloxane is affixed firmly to the surface of the powdered pigment, it is not necessarily the totality of functional groups that takes part in the adhesion to the surface of the powdered particle. That is, it may be predicted that, since steric hindrance is liable to occur due to the chain of the straight-chain of alkylpolysiloxane when the polymerization degree is 25 to 100, a portion of the functional groups is present in an unreacted state, or occasionally a portion of the functional groups react with each other to form the products thereof. The reactive alkylpolysiloxanes which could affix firmly to the surface of the powdered particules, do not contribute to the hydrophobic property and water-proofness of the surface-treated powders, and are easily eluted by washing with an organic solvent which can dissolve silicone oil.

Depending on the varieties of powdered pigment, the surfaces of the particles (the differences in the degree of surface activity and the distributions of the active sites) are much different, with resulting differences in the reactivity of the reactive alkoxypolysiloxane to the surface of the particles and the strength of adhesion. Thus, the desired hydrophobic properties or water-proofness could not necessarily be obtained in pearl pigments as the starting materials for cosmetic, such as hydrated yellow iron oxide, iron oxide, titanium oxide, titanium mica. Such problems can be overcome with the powdered base material treated with organic silicon compounds according to the present invention.

In the powdered pigments, the metal hydroxides, hydroxy group-containing inorganic oxides and the gelated products thereof function to make uniform and homogeneous the surface of the powdered pigments, and also at the same time, have the effects of improving much more their adhesion to the methylhydrogen polysiloxane and the reactive alkylpolysiloxane.

The methylhydrogen polysiloxane employed typically in the present invention, for example, KF9901 ( manufactured by SHIN-ETSU KAGAKU KK.), is a silicone oil which contains a low molecular silicone oil and has a broad or wide distribution of molecular weight. Accordingly, the ductility and osmosis of the low molecular silicone oil in the microscopic part in the powdered base materials and/or the powdered pigments is superior, in comparison to the reactive alkylpolysiloxane. For this reason, for example, the kinetics viscosity (cst) of the methylhydrogen polysiloxane employed typically in the present invention having the siloxane unit in the polymerization degree of 40 is around 15. In contrast, the kinetics viscosity (cst) of the reactive alkylpolysiloxane employed typically in the present invention is around 40. When the ductility and osmosis of the low molecular silicone oil in the microscopic parts in the powdered base material and/or the powdered pigment is high, the active sites (adhesion sites) present in the surface of the particles thereof and the functional groups come into mutual contact much more, and at the same time the coating film is formed in much more homogeneous state.

With respect to the number of functional groups per unit of the methyl hydrogen polysiloxane and the reactive alkylpolysiloxane employed typically in the present invention, the number in the methylhydrogen polysiloxane which has the functional groups in the side chain is much greater than the number in the reactive alkylpolysiloxane which has the functional groups only in one side of the tail end. For example, the methyl hydrogen polysiloxane with the polymerization degree of 40 wherein m:n=0.5:1 in the above-mentioned formula specified preferably in the present invention, has 27 of the functional groups in one polysiloxane chain. On the other hand, the reactive alkylpolysiloxane has the functional groups only in the tail end in one side, and thus it has 3 of the functional groups, for example, in the case the functional group is an alkoxy group.

For these reasons, when the particles are surface-treated with the methyl hydrogen polysiloxane and the reactive alkylpolysiloxane in the present invention, due to the high ductility and the high osmosis in the surface of the particles of the methyl hydrogen polysiloxane, the polysiloxanes reach microscopic parts of the particles, and they are reacted by the strength of shearing force from the stirring and by the action of heat from the heating, and the like, to form the homogeneous film, as surmised by the inventors.

On the other hand, the reactive methyl hydrogen polysiloxane is also contacted with the powdered base material and/or the powdered pigment on their surface, and the part which contacted the active sites in their surface reacts and fixes thereto. And, the functional groups which would not come into contact with the active sites, proceed to fix to the particles by self-condensations according to the following equations:
Reaction $$\text{Si—H} + \text{H}_2\text{O} \rightarrow \text{SiOH} + \text{H}_2 \quad [1]$$

$$\text{Si(OE)} + \text{H}_2\text{O} \rightarrow \text{SiOH} + \text{EOH} \quad [2]$$

$$[1](\text{SiOH}) + [2](\text{SiOH}) \rightarrow \text{Si—O—Si—} + \text{H}_2\text{O} \quad [3]$$

wherein "(OE)" denotes alkoxy group.

$$\text{Si—H} + \text{Si—H} + \text{O}_2 \rightarrow \text{Si—O—Si} + \text{H}_2\text{O} \quad [4]$$

$$\text{M·O·OH} + \text{SiH} \rightarrow \text{M—O—Si—} + \text{H}_2\text{O} \quad [5]$$

[6]

[7]

wherein "M" denotes metal atom.

With the pigment treated with the organic silicon compound disclosed in the above-mentioned patent publication, since the above-mentioned reactive alkyl polysiloxane is adhered with various degrees of adhesion to the pigment itself, and since the above-mentioned reactive alkyl polysiloxane has a varying adhesion degree from one production lot to another, the pigment is not shifted completely to the oily phase of the emulsion, but tends to be present on the interface between the oily phase and the aqueous phase of the emulsion. With time the pigment exhibiting stronger adhesion properties of the above-mentioned reactive alkyl polysiloxane shifts to the oily phase, while the pigment exhibiting only adhesion properties of the above-mentioned reactive alkyl polysiloxane shifts to the aqueous phase, causing problems in particular in emulsion, giving rise to color separation of the cream and liquid foundation. This problem can be solved with the powdered base material treated with organic silicon compounds of the present invention.

EXAMPLES

Figure 1:
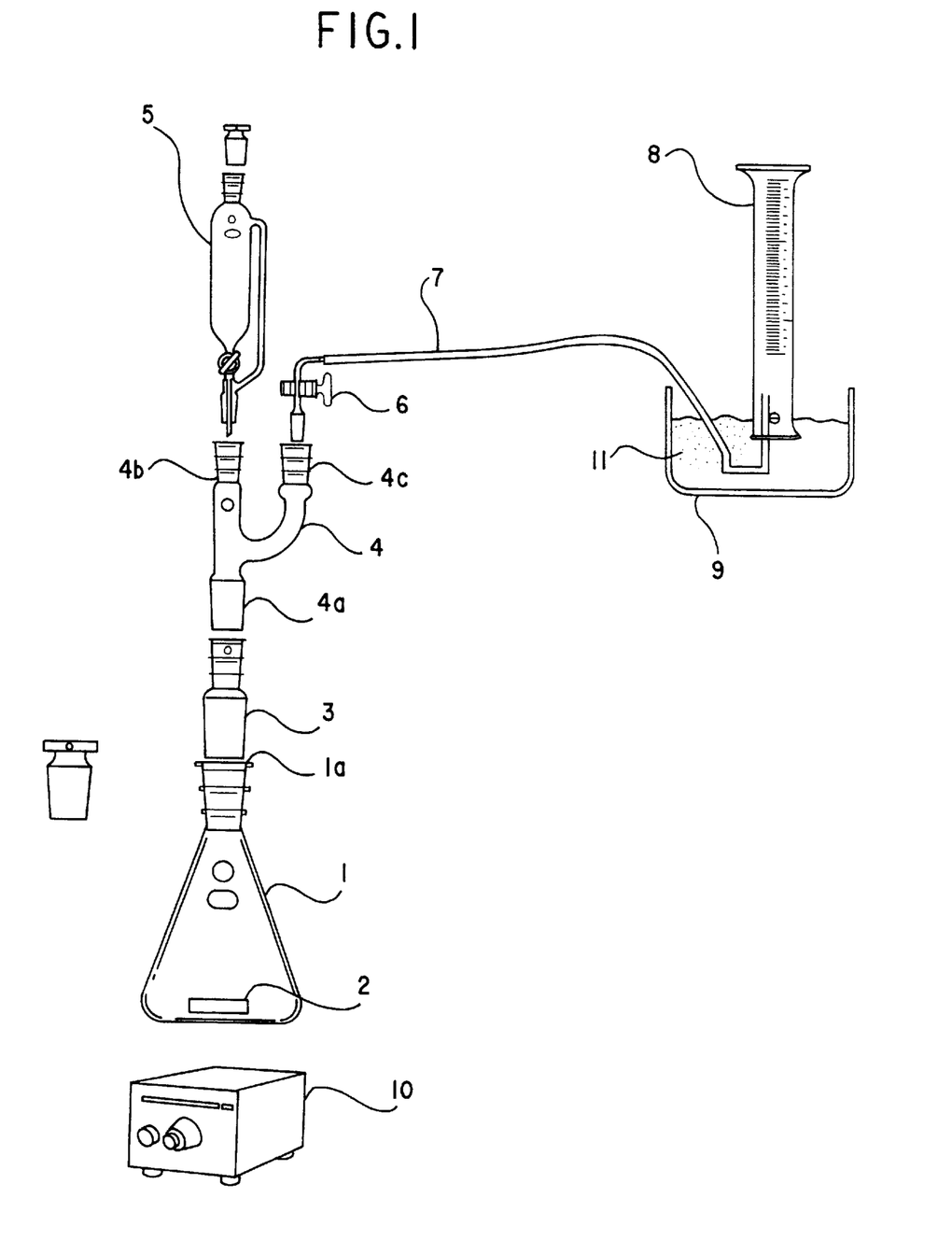
FIG. 1 is an exploded view of a residual hydrogen measurement device used in the invention.

The present invention will be explained in further details with reference to the following examples and comparative examples. FIG. 1 shows a residual hydrogen measurement device employed in the example of the present invention, wherein:

1 triangular flask with co-plug
2 agitator
3 joint of different diameter
4 Y-shaped tube
5 dripping funnel fitted with pressure cancellation tube
6 glass cock
7 silicon rubber tube
8 messcylinder
9 water vessel
10 magnetic stirrer
11 water.

EXAMPLE 1

To a solution obtained by dissolving 17.75 g of aluminum chloride in 800 ml of purified water, 20 g of sericite FSE manufactured by SANSHIN KOKO, and 80 g of titanium oxide A-100 manufactured by ISHIHARA SANGYO under agitation were added and dispersed homogeneously. To this liquid dispersion was added dropwise 300 ml of an aqueous solution of 8.81 g sodium hydroxide. After the end of dropwise addition, the reaction system was agitated and cured for one hour, filtered and washed with water to yield a powdery product, which was then crushed with a crusher. To the resulting crushed product was added dropwise a solution obtained by dissolving in 50 ml of iso-propanol, 3.0 g of α-triethoxy polydimethyl polysiloxane (polymerization degree of 30, molecular weight dispersion degree of 1.19 with a terminal group which is an ethoxy group) and 0.5 g of methyl hydrogen polysiloxane having a specified proportion of the dimethyl polysiloxane units and a specified polymerization degree according to the present invention, with m=7 and n=14 in the above-mentioned formula specified preferably for the present invention. The resulting solution was agitated for one hour. The powders, thus treated, were then treated for five hours in a hot air drier maintained at 140, in order to obtain a novel pigment treated with organic silicon compounds.

Comparative Example 1 -1

The procedure of Example 1 was followed except for not using the above-mentioned methyl hydrogen polysiloxane of Example 1.

Comparative Example 1-2

The procedure of Example 1 was followed except for not using the above-mentioned α-triethoxy polydimethyl polysiloxane of Example 1.

EXAMPLE 2

To a solution obtained by dissolving 31.53 g of magnesium chloride in 800 ml of purified water were added 20 g of talc JA46A manufactured by ASADA SEIFUN KK and 80 g of mapico yellow lemon manufactured by TITAN KOGYO KK and dispersed homogeneously. To this liquid dispersion was add dropwise 300 ml of an aqueous solution of 12.40 g sodium hydroxide. After the end of dropwise addition, the reaction system was agitated and cured for one hour, filtered and washed with water to yield a powdery product, which was then crushed with a crusher. To the resulting crushed product was added dropwise a solution obtained by dissolving in 30 ml of xylene, 6 g of α-monohydroxy siloxane (polymerization degree of 50, molecular weight dispersion degree of 1.21 with a terminal group which is a monosilanol group) and 2.5 g of methyl hydrogen polysiloxane having a specified proportion of the dimethyl polysiloxane units and a specified polymerization degree according to the present invention, with m=5 and n=15 in the above-mentioned formula specified preferably for the present invention. The resulting solution was agitated for one hour. The powders, thus treated, were then treated for four hours in a vacuum drier maintained at 115 for heating polymerization, in order to obtain a novel pigment treated with organic silicon compounds.

Comparative Example 2-1

The procedure of Example 2 was followed except for not using the above-mentioned methyl hydrogen polysiloxane of Example 2.

Comparative Example 2-2

The procedure of Example 2 was followed except for not using the above-mentioned α-monohydroxy siloxane of Example 2.

EXAMPLE 3

The procedure of Example 1 was followed except for using 20 g of talc manufactured by HAYASHI KASEI KK instead of 20 g of sericite FSE manufactured by SANSHIN KOKO and using 80 g of Iron oxide red hippo manufactured by MORISHITA BENGARA KK instead of 80 g of titanium oxide A-100 manufactured by ISHIHARA SANGYO, respectively, of Example 1.

Comparative Example 3-1

The procedure of Example 3 was followed except for not using the above-mentioned methyl hydrogen polysiloxane of Example 1 used in Example 3.

Comparative Example 3-2

The procedure of Example 3 was followed except for not using α-triethoxy polydimethyl polysiloxane of Example 1 used of Example 3.

EXAMPLE 4

The procedure of Example 1 was followed except for using 100 g of sericite FSE manufactured by SANSHIN KOKO instead of 20 g of sericite FSE manufactured by SANSHIN KOKO and 20 g of talc manufactured by HAYASHI KASEI KK and also except for using α-trimethoxy polydimethyl siloxane (polymerization degree of 35 and molecular weight dispersion degree of 1.20, wherein one of terminal groups is a methoxy group) instead of α-triethoxy polydimethylsiloxane, respectively, of Example 1.

Comparative Example 4-1

The procedure of Example 4 was followed except for not using the above-mentioned methyl hydrogen polysiloxane of Example 1 used in Example 4.

Comparative Example 4-2

The procedure of Example 4 was followed except for not using the above-mentioned a-trimethoxy polydimethyl siloxane.

EXAMPLE 5

Powder Foundation

| | Numeric value: parts by weight |
|---|---|
| Component A | |
| novel sericite treated with organic silicon compounds (Ex. 4) | 55.6 |
| novel titanium oxide treated with organic silicon compounds (Ex. 1) | 10.0 |
| nylon powders | 13.0 |
| novel mapico yellow lemon treated with organic silicon compounds (Ex. 2) | 3.5 |
| iron oxide red "shippo" treated with organic silicon compounds (Ex. 3) | 1.6 |
| methyl paraben | 0.2 |
| Component B | |
| squalane | 4.0 |
| methyl polysiloxane | 6.0 |
| octyl dodecyl myristate | 4.0 |
| sorbitan monooleate | 2.0 |
| α- δ- tocopherol | 0.05 |
| perfume | 0.05 |

The component A was charged into a Henschel mixer for mixing for three minutes. To the resulting mixture, the component B, previously mixed homogeneously and dissolved, was gradually added and mixed continuously for ten minutes. The resulting mixture was crushed by a crusher and passed through a blower sifter. The resulting mass was press-charged to give a product.

Comparative Example 5

Powder Foundation

The procedure of Example 5 was followed except for using the pigment treated with the organic silicon compounds of Comparative Example 4-1, Comparative Example 1-1, Comparative Example 2-1 and Comparative Example 3-1 in place of the novel pigment treated with the organic silicon compounds of the component A of Example 5, looking from the uppermost side.

EXAMPLE 6

O/W Foundation

| | Numeric value: parts by weight |
|---|---|
| Component A | |
| squalane | 3.0 |
| methylphenyl polysiloxane | 0.5 |
| tri-2-ethyl hexanoic acid glycerin | 6.0 |
| mink oil | 1.5 |
| purified lanolin | 1.5 |
| cetyl alcohol | 0.8 |
| butyl alcohol | 0.7 |
| candelilla wax | 1.0 |
| stearic acid | 1.5 |
| monostearic acid glycerin | 0.75 |
| monostearic acid polyoxyethylene sorbitan | 1.75 |

-continued

O/W Foundation

| | Numeric value: parts by weight |
|---|---|
| monolauric acid polyoxyethylene sorbitan | 0.5 |
| sesqui oleic acid sorbitan | 0.5 |
| novel pigment iron oxide red treated with organic silicon compounds (Ex. 3) | 0.63 |
| novel mapico yellow lemon treated with organic silicon compounds (Ex. 2) | 2.10 |
| novel titanium oxide treated with organic silicon compounds (Ex. 1) | 9.0 |
| novel sericite treated with organic silicon compounds (Ex. 4) | 6.0 |
| Component B | |
| magnesium aluminum silicate | 0.5 |
| titanium mica | 1.0 |
| 1,3 butylene glycol | 6.0 |
| xanthane gum | 0.05 |
| carboxy methyl cellulose sodium | 0.1 |
| methyl paraben | 0.2 |
| triethanol amine | 0.95 |
| perfume | 0.1 |
| purified water | 54.37 |

After the component A was heated to 90° C. for dissolution and dispersion, the component B heated to 85° C. was added to the resulting dispersion and the resulting mixture was emulsified at 85° C. The resulting mass was cooled to 30° C. and charged as a product into a vessel.

Comparative Example 6

The procedure of Example 6 was followed except for using the pigment treated with the organic silicon compounds of Comparative Example 3-1, Comparative Example 2-1, Comparative Example 1-1 and Comparative Example 4-1 in place of the novel pigment treated with organic silicon compounds of the components A of the Example 6, looking from the uppermost side.

EXAMPLE 7

Under-Makeup Base

| | Numeric value: parts by weight |
|---|---|
| Component A | |
| bees wax | 1.0 |
| cetyl alcohol | 1.0 |
| cetyl octanoate | 1.0 |
| squalane | 10.5 |
| monostearic acid polyethylene glycol | 1.7 |
| monostearic acid sorbitan | 2.8 |
| butyl paraben | 0.1 |
| novel iron oxide red treated with organic silicon compounds (Ex. 3) | 2.1 |
| novel mapico yellow lemon treated with organic silicon compounds (Ex. 2) | 0.9 |
| novel titanium oxide treated with organic silicon compounds (Ex. 1) | 3.0 |
| Component B | |
| propylene glycol | 8.0 |
| 1% carboxy vinyl polymer | 20.0 |
| xanthane gum | 0.1 |
| methyl paraben | 0.2 |
| purified water | 47.5 |
| perfume | 0.1 |

The component A was heated and dissolved at 85° C., and the component B heated to 85° C. was added thereto. The resulting mass was emulsified at 80° C. The emulsified product was cooled to 30° C. and charged as a product into a vessel.

Comparative Example 7

The procedure of Example 7 was followed except for using the pigment treated with the organic silicon compounds of Comparative Example 3-1, Comparative Example 2-1 and Comparative Example 1-1 in place of the component A of Example 7, looking from the uppermost side.

TABLE 1

| SAMPLES | HYDROPHOBIC PROPERTIES | WATER-PROOFNESS | FEELING TO TOUCH | ADHESION TO SKIN | RESIDUAL HYDROGEN |
|---|---|---|---|---|---|
| EX.1 | 5 | EXCELLENT | 5.6 | 6.0 | NOT MORE THAN DETECTION THRESHOLD OF 0.1 ml/g |
| COMP. EX.1-1 | 4 | GOOD | 5.0 | 5.9 | |
| EX.2 | 5 | EXCELLENT | 5.9 | 5.8 | |
| COMP. EX.2-1 | 1 | BAD | 5.1 | 5.6 | |
| EX.3 | 5 | EXCELLENT | 5.8 | 5.9 | |
| COMP. EX.3-1 | 3 | BAD | 5.0 | 5.8 | |
| EX.4 | 5 | EXCELLENT | 6.0 | 5.6 | |
| COMP. EX.4-1 | 3 | BAD | 5.8 | 5.2 | |

TABLE 2

MEASUREMENT OF DYNAMIC FRICTIONAL COEFFICIENT

| SAMPLES | MEAN FRICTIONAL COEFFICIENT MIU (=$10^{-1}$) |
|---|---|
| EX.1 | 5.21 |
| COMP. EX.1-1 | 5.47 |
| COMP. EX.1-2 | 7.09 |
| EX.2 | 5.04 |
| COMP. EX.2-1 | 5.56 |
| COMP. EX.2-2 | 6.48 |
| EX.3 | 5.13 |
| COMP. EX.3-1 | 5.65 |
| COMP. EX.3 | 6.57 |
| EX.4 | 4.85 |
| COMP. EX.4 | 4.80 |
| COMP. EX.4-2 | 6.08 |

It is seen from Tables 1 and 2 that the novel pigment treated with organic silicon compounds of the present invention is superior in hydrophobic properties and in water-proofness. Also, the pigment exhibited the feeling to the touch and adhesion to the skin equivalent or superior to those of the conventional pigments treated with the conventional organic silicon compound (pigment treated with reactive alkyl polysiloxane). On the other hand, the novel pigment showed a smaller dynamic frictional coefficient and a smoother skin touch than those of methyl hydrogen polysiloxane having a specified polymerization degree and a specified proportion of dimethyl polysiloxane unit. Moreover, the amount of residual hydrogen is smaller than the limit of equipment measurement and compares favorably with the conventional pigment treated with the organic silicon compound.

TABLE 3

| SAMPLES | FEELING TO TOUCH | QUALITY STABILITY ROOM TEMPERATURE | 40° C. | DURABILITY OF ADHESION TO SKIN |
|---|---|---|---|---|
| EX.5 | 5.9 | | | 5.8 |
| COMP. EX.5 | 5.4 | | | 5.0 |
| EX.6 | 5.8 | COLOR | SEPARATION | 5.7 |
| COMP. EX.6 | 4.0 | SEPARATION | | 4.1 |
| EX.7 | 5.8 | COLOR | COLOR | 5.9 |
| COMP. EX.7 | 4.2 | SEPARATION | SEPARATION | 4.7 |

It is seen from the results of Table 3 that mixing the novel powders treated with organic silicon compounds according to the present invention into cosmetic gives a cosmetic superior in quality stability, skin feeling to the touch, and in durability in adhesion of cosmetic.

The method for evaluating the hydrophobic properties, feeling to the touch, adhesion to skin, residual hydrogen, quality stability and the dynamic frictional coefficient, is as follows:

Evaluation of Hydrophobic Properties 10 ml of purified water was weighed out in a test tube of 30 ml in capacity and 0.1 g of a sample was precisely weighed out and charged into it. The test tube was stirred strongly by hand and allowed to settle. The hydrophobic properties were evaluated in terms of turbidity after five minutes. The standards for evaluation were as follows:

5 . . . powders collect on the gas-liquid interface, with the aqueous phase being transparent.

4 . . . powders collect on the gas-liquid interface, with the aqueous phase being slightly turbid.

3 . . . powders are partially precipitated, with the aqueous phase being slightly turbid.

2 . . . powders partially float in the aqueous phase, but the major portion of the powders are precipitated.

1 . . . powders are precipitated in their entirety.

Evaluation of Water-Proofness

In a transparent screw-tap vial (with a capacity of 50 ml) manufactured by NICHIDEN GLASS KK, 20 g of purified water and 20 g of decamethyl cyclopentane siloxane, manufactured by TORAY DOW CORNING under the trade name of SH245, were weighed out and charged. In the resulting mass was added 0.1 g of a precisely weighed out sample. The liquid mixture of purified water and decamethyl cyclopentane siloxane, with the sample added, was strongly agitated by hand ten times and allowed to settle for three days in a constant-temperature room maintained at 50. When taken out from the constant-temperature room, the liquid mixture with the sample was agitated strongly by hand ten times and allowed to settle before observing the state of the interface between the purified water and decamethyl cyclopentane siloxane. The standard for evaluation was as follows:

Excellent . . . the sample is present as a beautiful homogeneous, monomolecular-like film on the interface between decamethyl cyclopentane siloxane and water.

Good . . . although the sample film present in the interface between decamethyl cyclopentane siloxane and water is a beautiful homogeneous, monomolecular-like film, the film is sagged (the interfacial film is sagged more prominently than the film specified in "Excellent" above).

Acceptable . . . the sample on the interface between purified water and decamethyl cyclopentane siloxane entrained water, thus presenting an irregular non-homogeneous film.

Bad . . . the state of the interface between the purified water and decamethyl cyclopentane siloxane is irregular and non-homogeneous, with part or all of the sample being precipitated.

Evaluation of Feeling to Touch and Feeling in Use (Adhesion to Skin and Durability of Adhesion to Skin)

A functional test was conducted by 11 functional test panelists. The standards for evaluation were as follows:
6 . . . excellent
5 . . . extremely good
4 . . . pretty good
3 . . . good
2 . . . rather good
1 . . . slightly good
0 . . . bad Test for Measuring Residual Hydrogen The residual hydrogen was determined using a residual hydrogen measurement device manufactured by MIYOSHI KASEI, INC., shown in exploded view in FIG. 1.

The amount of the residual hydrogen is calculated as follows:

residual hydrogen (ml/g)=(amount of the evolved gas–blank value)/amount of sample.

10 g of the sample was weighed out precisely and put in a triangular flask 1 having a capacity of 500 ml fitted with a co-plug. In this flask 1 were charged 30 ml of xylene and an agitator 2 ( length of 70 mm and a diameter of 15 mm) for agitation at a pre-set rate for one minute with a magnetic stirrer 10. Then, 20 ml of a KOH/ ethanol solution (KOH concentration of 1 wt %) were added into the triangular flask fitted with the co-plug from a dripping funnel fitted with a pressure cancellation tube 5 (capacity of 100 ml), and the resulting solution was stirred further for one minute. The gas evolved at this time was collected in a messcylinder 8 with the capacity of 100 ml. The amount of the gas evolved was read with the messcylinder. In this case, an opening end 1a of the triangular flask is connected via a joint with different diameter 3 to a branched pipe 4a of a Y-shaped tube 4. The above-mentioned KOH/ethanol solution was added to the triangular flask fitted with the co-plug via another branched pipe 4b of the bifurcated Y-shaped tube 4. From the other branched tube 4c of the above-mentioned bifurcated Y-shaped tube, hydrogen gas was collected via a glass cock 6 and a silicone rubber tube 7 with an inner diameter of 3 mm into the messcylinder with the opening end directed along the direction of the force of gravity in the water vessel 9 and which was filled with water 11.

Quality Stability

The quality stability in two years at room temperature and in three months at a temperature of 40° C., respectively was evaluated. In Table 3, ⊚ indicates that there is no change in viscosity or hardness of the product over time, with no color separation, color shading, water separation, or the like.

Measurement of Dynamic Frictional Coefficients

The dynamic frictional coefficient was measured using a sensor (KES-SE, FRICTION TESTER, manufactured by KATOTEC KK).

Specifically, a double-sided tape was stuck to a slide glass, and a powdered sample was dropped thereon. Any excess sample was wiped off with a finger. A sensor was slid on the powdered sample. Table 2 shows a mean value over 20 mm of the frictional coefficient $\mu$ as mean frictional coefficient (MIU). The measurement conditions were as follows:

| Conditions for Measurements | |
|---|---|
| Force Sensitivity | H (Force sum 20 g/V) |
| Sliding Speed | 0.5 mm/sec |
| Static Frictional Load | 25 g |
| Friction Sensor | silicon sensor |

Effect of the Invention

Since a powdered base material treated with organic silicon compounds according to the invention is comprised of a reactive alkyl polysiloxane and the above-mentioned specified methyl hydrogen polysiloxane affixed to a powdered base material, the characteristics of a reactive alkyl polysiloxane are retained while improving hydrophobic properties and water-proofness, which were weak points of the alkyl polysiloxane.

The method for production in the claimed invention comprises the step of thermally reacting a powdered base material with a reactive alkyl polysiloxane and a methyl hydrogen polysiloxane as described above, preferably the methyl hydrogen polysiloxane represented by the above-mentioned formula (1), whereby the reactive alkyl polysiloxane and the methyl hydrogen polysiloxane are affixed to the powdered base material, and the powdered base material treated with organic silicon compounds according to the present invention can be produced readily.

The cosmetic comprising the above-defined powdered base material treated with organic silicon compounds of the present invention, is superior in quality stability and feeling of the skin to the touch.

What is claimed is:

1. A powdered base material treated with organic silicon compounds, comprising a powdered base material thermally reacted with a reactive alkyl polysiloxane in the presence of a methyl hydrogen polysiloxane, whereby said reactive alkyl polysiloxane and said methyl hydrogen polysiloxane are fixed on the surfaces of the powdered base material, and wherein said methyl hydrogen polysiloxane is at least one selected from the group consisting of compounds represented by the following formula (2):

$$(CH_3)_3SiO[(CH_3)_2SiO]_m(CH_3HSiO)_nSi(CH_3)_3 \qquad (2)$$

wherein m and n are each an integer, m+n=7 to 50 and m:n=1:0.2 to 1:4, and compounds represented by the following formula (3):

$$(CH_3)_3SiO[(CH_3)_2SiO]_m(CH_3SiO)_nSi(CH_3)_3 \qquad (3)$$

wherein m and n are each an integer, m+n=7 to 25 and m:n=1:0.5 to 1:2.

2. The powdered base material treated with organic silicon compounds as defined in claim 1, wherein said methyl hydrogen polysiloxane is represented by the following formula (2):

$$(CH_3)_3SiO[(CH_3)_2SiO]_m(CH_3HSiO)_nSi(CH_3)_3 \qquad (2)$$

wherein m and n are each an integer, m+n=7 to 50 and m:n=1:0.2 to 1:4.

3. The powdered base material treated with organic silicon compounds as defined in claim 1, wherein said methyl hydrogen polysiloxane is represented by the following formula (3):

$$(CH_3)_3SiO[(CH_3)_2SiO]_m(CH_3HSiO)_nSi(CH_3)_3 \qquad (3)$$

wherein m and n are each an integer, m+n=7 to 25 and m:n=1:0.5 to 1:2.

4. The powdered base material treated with organic silicon compounds as defined in claim 1 or 2, wherein said powdered base material is a compound powdered base material comprised of at least one substance selected from the group consisting of metal hydroxides, hydroxy group-containing inorganic oxides and the gelated products thereof fixed to a powdered base material.

5. The powdered base material treated with organic silicon compounds as defined in claim 1, wherein said reactive alkyl polysiloxane is a straight-chained reactive alkyl polysiloxane having a polymerization degree of 25 to 100 and a ratio (Mw/Mn) of the weight average molecular weight (Mw) to the number average molecular weight (Mn) of 1.0 to 1.3, and having at one of the terminals of the molecular chain at least one of an alkoxy group, a hydroxy group, a halogen atom, an amino group and an imino group.

6. The powdered base material treated with organic silicon compounds as defined in claim 1, wherein a ratio (H/F) of the weight (H) of said reactive alkyl polysiloxane to the weight (F) of said powdered base material ranges between 0.1/100 and 30/100.

7. The powdered base material treated with organic silicon compounds as defined in claim 1, wherein a ratio (M/F) of the weight (M) of said methyl hydrogen polysiloxane to the weight (F) of said powdered base material ranges between 0.1/100 and 5/100.

8. The powdered base material treated with organic silicon compounds as defined in claim 4, wherein a ratio (K/F) of the total weight (K) of the metal hydroxide(s), the hydroxy group-containing inorganic oxide(s) and/or the gelated product(s) thereof fixed in said compound powdered base material to the weight (F) of said powdered base material ranges between 0.1/100 and 10/100.

9. A method for producing a powdered base material treated with organic silicon compounds as defined in claim 1 or 2, comprising the step of thermally reacting a reactive alkyl polysiloxane and a methyl hydrogen polysiloxane with a powdered base material, to give a powdered base material to which said reactive alkyl polysiloxane and said methyl hydrogen polysiloxane are fixed.

10. A cosmetic comprising the powdered base material treated with organic silicon compounds as defined in claim 1 or 2.

11. The powdered base material treated with organic silicon compounds as defined in claim 1, wherein said reactive alkyl polysiloxane is a straight-chain reactive alkyl polysiloxane having a polymerization degree of 25 to 100 and a ratio (Mw/Mn) of the weight average molecular weight (Mw) to the number average molecular weight (Mn) of 1.0 to 1.3, and having at one of the terminals of the molecular chain at least one of an alkoxy group, a hydroxy group, a halogen atom, an amino group and an imino group.

* * * * *

UNITED STATES PATENT AND TRADEMARK OFFICE
CERTIFICATE OF CORRECTION

PATENT NO. : 6,200,580 B1
DATED : March 13, 2001
INVENTOR(S) : Horino et al.

Page 1 of 1

It is certified that error appears in the above-identified patent and that said Letters Patent is hereby corrected as shown below:

Column 22,
Line 48, should read
-- $(CH_3)_3SiO[(CH_3)_2SiO]_m(CH_3HSiO)_nSi(CH_3)_3$     (3) --

Signed and Sealed this

Sixteenth Day of October, 2001

Attest:

NICHOLAS P. GODICI
Attesting Officer      Acting Director of the United States Patent and Trademark Office